US00PP33026P2

(12) United States Plant Patent
van Langen

(10) Patent No.: US PP33,026 P2
(45) Date of Patent: May 4, 2021

(54) ***HAWORTHIA* HYBRID PLANT NAMED 'AMIHAW1911'**

(50) Latin Name: ***Haworthia limifolia* x *Aloe vera***
Varietal Denomination: AMIHAW1911

(71) Applicant: NovoAmi B. V., Heerhugowaard (NL)

(72) Inventor: Gerard van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 16/895,245

(22) Filed: Jun. 8, 2020

(30) Foreign Application Priority Data

Dec. 6, 2019 (QZ) ..... 2019/3322

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — Samuel R. McCoy, Jr.

(57) ABSTRACT

A new and distinct *Haworthia* hybrid plant named 'AMIHAW1911', which is characterized by spirally-arranged, dark green foliage with small light green orbicular protuberances arranged in irregular transverse rows on the lower leaf surfaces and small near-white teeth along the length of the margins. The new variety has shown to be uniform and stable in the resulting generations from asexual propagation.

4 Drawing Sheets

Latin name of the genus and species: The Latin name of the genus and species of the novel variety disclosed herein is *Haworthia limifolia* x *Aloe vera*.

Variety denomination: The inventive variety of *Haworthia* hybrid disclosed herein has been given the variety denomination 'AMIHAW1911'.

CROSS REFERENCE TO RELATED APPLICATIONS

This application claims priority to the Community Plant Variety Rights application number 2019/3322, filed Dec. 6, 2019, which is herein incorporated by reference.

BACKGROUND OF THE INVENTION

Parentage: 'AMIHAW1911' is a spontaneous whole-plant mutation of *Haworthia limifolia* x *Aloe vera* 'AMIHAW1613' (U.S. Plant Pat. No. 31,419) which was discovered in the autumn of 2018 at a commercial greenhouse in Heerhugowaard, the Netherlands. The mutation was noted for its dark green foliage that is sparsely covered with transverse rose of foliar protuberances. After confirming the stability of the unique characteristics first observed, the new plant was selected for commercialization and given the name, 'AMIHAW1911'.

Asexual Reproduction: Asexual reproduction of the new cultivar 'AMIHAW1911', by way of rooting leaf cuttings, was first initiated in the winter of 2018 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIHAW1911' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIHAW1911'. These characteristics in combination distinguish 'AMIHAW1911' as a new and distinct *Haworthia* hybrid cultivar:

1. 'AMIHAW1911' exhibits succulent foliage that is spirally-arranged in a basal rosette; and
2. 'AMIHAW1911' exhibits dark green foliage with small, near-white teeth along the length of the margins; and
3. 'AMIHAW1911' exhibits an adaxial leaf surface which is very sparsely covered with small orbicular protuberances; and
4. 'AMIHAW1911' exhibits an adaxial leaf surface that is sparsely covered with small orbicular protuberances arranged in irregular transverse rows and one irregular yet distinct longitudinal row along the distal centerline.

BOTANICAL DESCRIPTION OF THE PLANT

Figure 1:
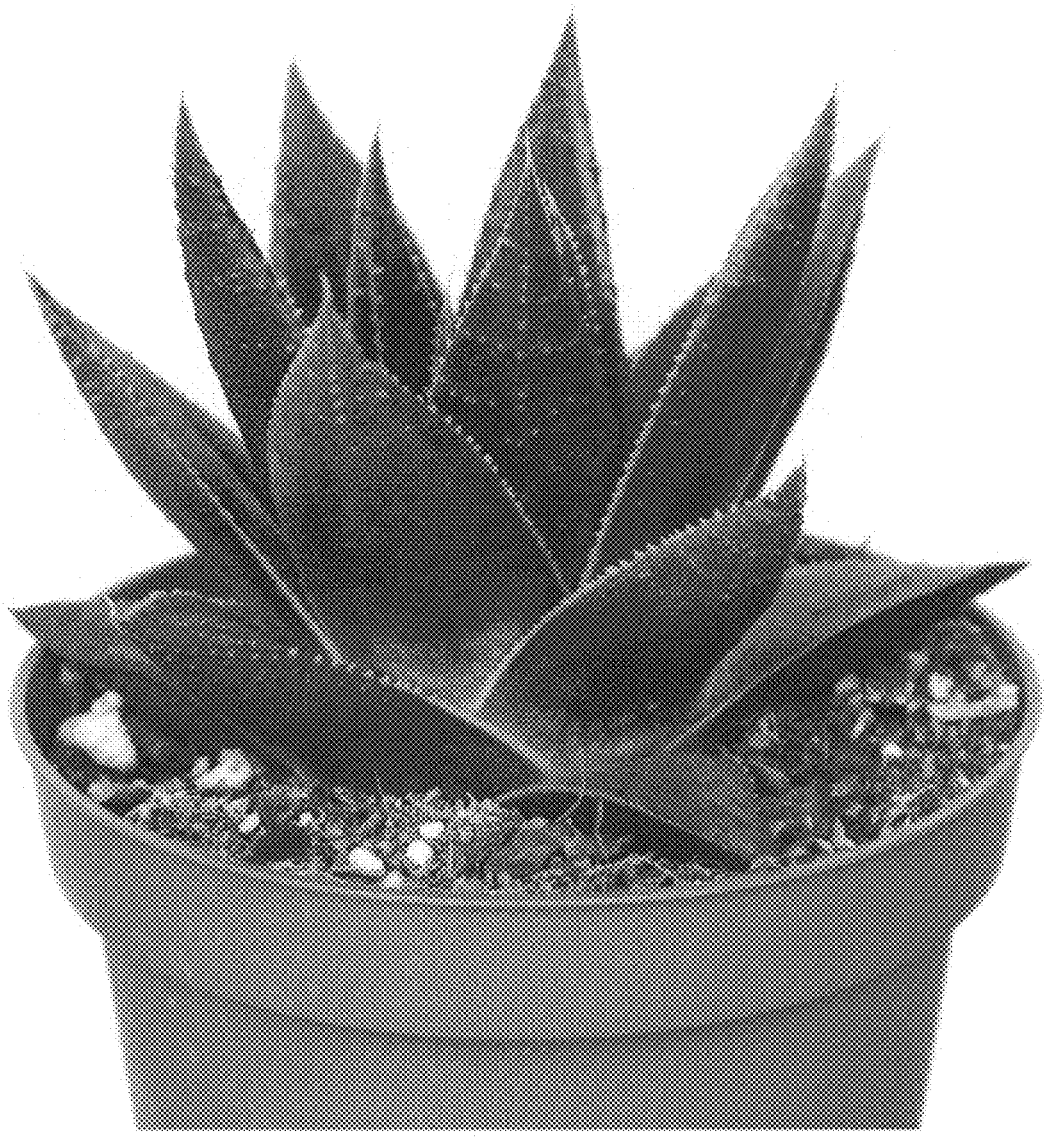
FIG. 1 illustrates, as nearly true as it is reasonably possible to make the same in color photographs of this type, an exemplary plant of 'AMIHAW1911' grown in a commercial greenhouse in Heerhugowaard, the Netherlands. This plant is approximately 1 year old, shown planted in an 11 cm container.
Figure 2:
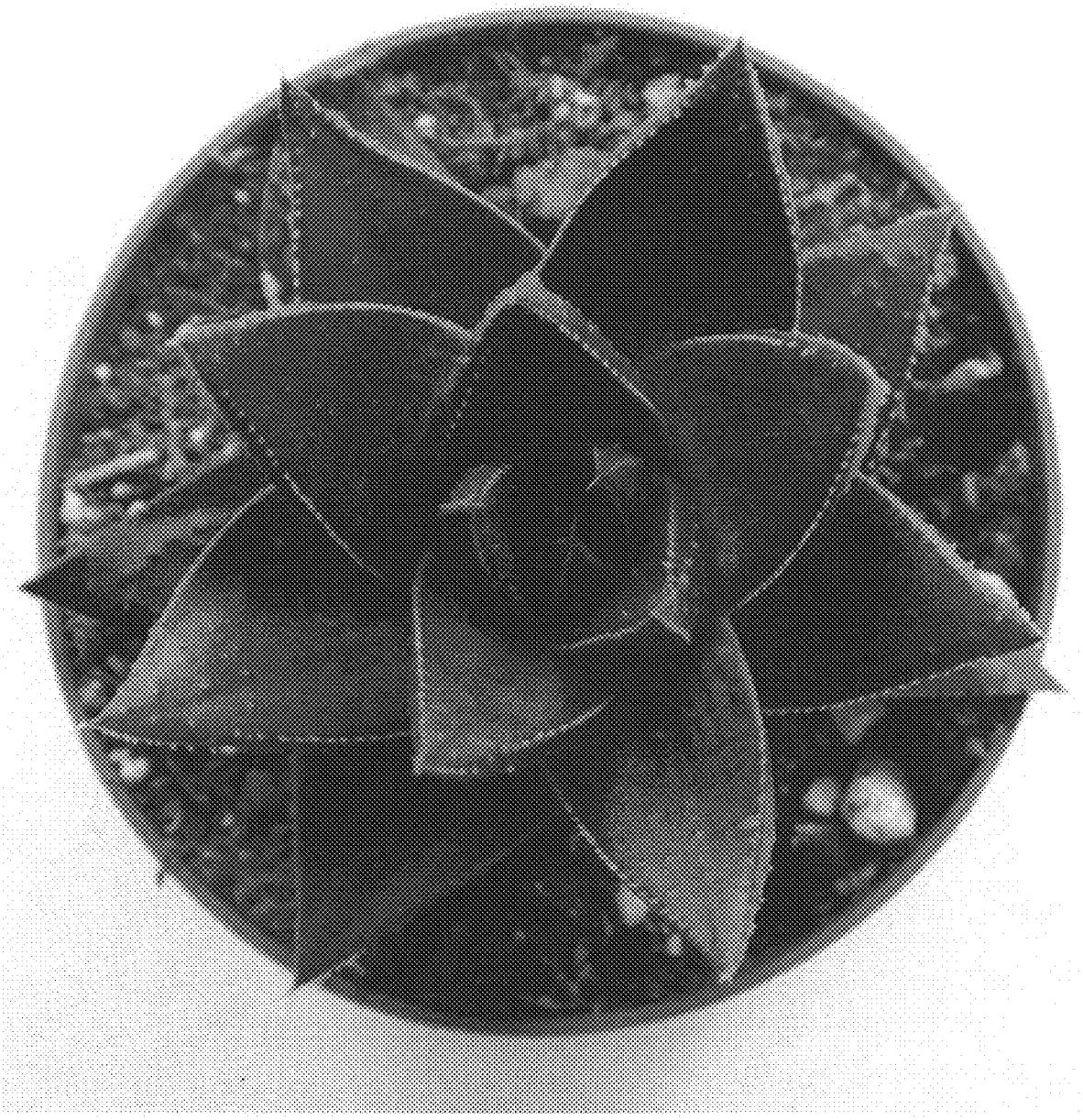
FIG. 2 illustrates, as nearly true as it is reasonably possible to make the same in color photographs of this type, the typical foliage arrangement of 'AMIHAW1911'.
Figure 3:
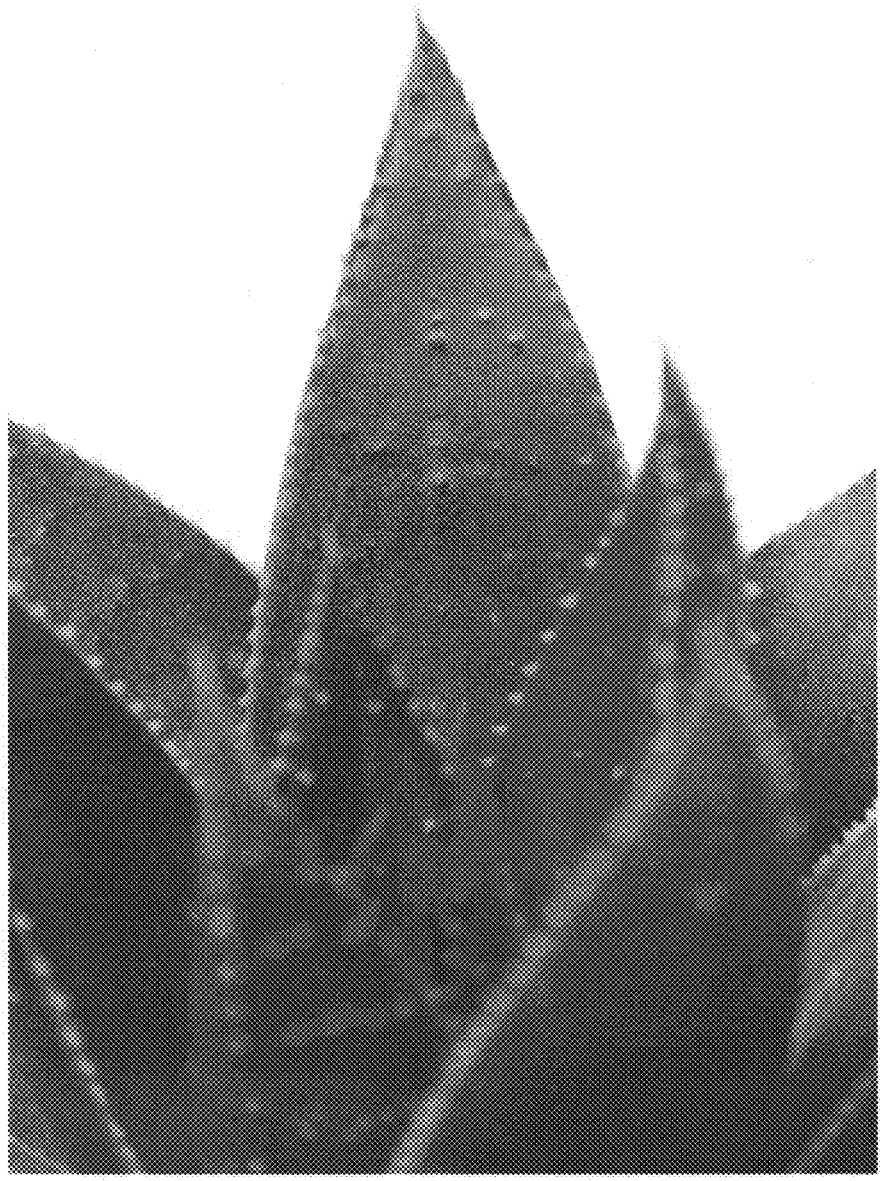
FIG. 3 illustrates, as nearly true as it is reasonably possible to make the same in color photographs of this type, the adaxial surface of the mature foliage 'AMIHAW1911'.
Figure 4:
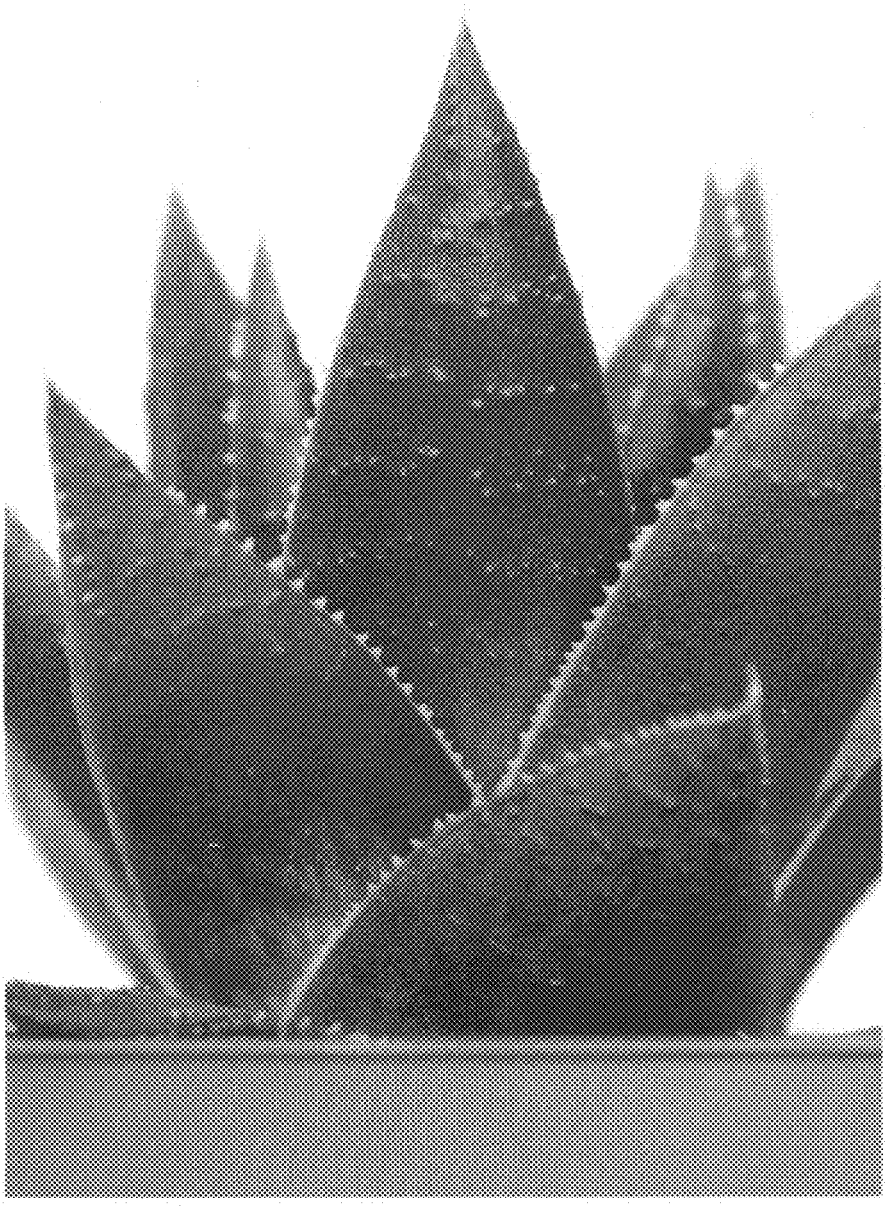
FIG. 4 illustrates, as nearly true as it is reasonably possible to make the same in color photographs of this type, the abaxial surface of the mature foliage 'AMIHAW1911'.

The following observations and measurements made in January of 2020 describe averages from a sample set of six specimens of 1 year-old 'AMIHAW1911' plants grown in 11 cm nursery containers at commercial greenhouse in Heerhugowaard, the Netherlands. Plants were produced using conventional greenhouse production protocols for *Haworthia* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIHAW1911' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIHAW1911' and a comparison with the parent and closest known comparator is provided below.

Plant description:

*Growth habit*.—Succulent perennial with foliage growing in a stemless, non-branched basal rosette.

*Plant shape*.—Globular.

*Height from soil level to top of foliar plane*.—8.1 cm.

*Plant spread*.—Average of 10.2 cm.

*Growth rate*.—Slow to moderately fast.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 9 cm container.

*Disease and pest resistance or susceptibility*.—Neither resistance nor susceptibility to typical *Haworthia* or *Aloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally arranged in a rosette.

*Division*.—Simple.

*Attachment*.—Sessile.

*Quantity*.—21 leaves per rosette.

*Shape*.—Ovate to narrowly ovate, succulent foliage.

*Dimensions*.—7.0 cm long, 3.0 cm wide, and 0.9 cm thick, on average.

*Aspect*.—Very slightly concave.

*Attitude*.—Juvenile foliage at the center of the rosette is held upward; foliage becomes progressively more relaxed towards the outer whorls of mature foliage, at an average angle of 52.5 degrees from horizontal.

*Apex*.—Apiculate, with a soft mucronate tip.

*Base*.—Broad cuneate.

*Margin*.—Finely dentate; teeth have an average length of 0.05 cm and are colored green-white, nearest to RHS 157D. Margins are not undulated or lobed.

*Texture, adaxial surface*.—Glabrous and very sparsely covered with small orbicular protuberances; protuberances are approximately 0.075 cm high and 0.075 cm in diameter, at maturity.

*Texture, abaxial surface*.—Glabrous and sparsely covered with small orbicular protuberances arranged in irregular transverse rows across the leaf surface and one irregular yet distinct longitudinal row along the distal centerline; protuberances are approximately 0.075 cm high and 0.075 cm in diameter, at maturity.

*Luster, adaxial surface*.—Moderately glossy.

*Luster, abaxial surface*.—Slightly to moderately glossy.

*Color*.—Juvenile foliage, adaxial surface — Nearest to in between green and yellow-green, RHS NN137A and 147A, and fading to yellow-green towards the base, nearest to RHS 145C; protuberances are colored greyed-green, nearest to a mixture of RHS 191C and 191D. Juvenile foliage, abaxial surface — Green, nearest to RHS NN137A, and fading to yellow-green towards the base, nearest to RHS 145C; protuberances are colored greyed-green, nearest to a mixture of RHS 191C and 191D. Mature foliage, adaxial surface — Nearest to in between green and yellow-green, RHS NN137A and 147A; fading to light yellow-green towards the base, nearest to RHS 148D; protuberances are colored in between yellow-green and greyed-green, RHS 147A and N189A, and tipped greyed-green, nearest to a mixture of RHS 191C and 191D. Mature foliage, abaxial surface — Nearest to in between green and yellow-green, RHS NN137A and 147A; fading to light yellow-green towards the base, nearest to RHS 148D; protuberances are colored in between yellow-green and greyed-green, RHS 147A and N189A, and tipped greyed-green, nearest to a mixture of RHS 191C and 191D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR:

Plants of the new cultivar 'AMIHAW1911' differ from the parent, *Haworthia limifolia* x *Aloe vera* 'AMIHAW1613' (U.S. Plant Pat. No. 31,419), in the following characteristics described in Table 1 below.

TABLE 1

| Characteristic | 'AMIHAW1911' | 'AMIHAW1613' |
|---|---|---|
| Abundance of foliage. | Less abundant than 'AMIHAW1613'. | More abundant than 'AMIHAW1911'. |
| Foliage size. | Smaller than 'AMIHAW1613'. | Larger than 'AMIHAW1911'. |
| Foliage thickness. | Thinner than 'AMIHAW1613'. | Thicker than 'AMIHAW1911'. |
| General coloration of the mature foliage. | Dark green. | Light greyed-green. |
| Abundance of foliar protuberances. | Less abundant than 'AMIHAW1613'. | More abundant than 'AMIHAW1911'. |

COMPARISONS WITH THE CLOSEST KNOWN COMPARATOR:

Plants of the new cultivar 'AMIHAW1811' differ from the closest known commercial comparator, *Haworthia* hybrid 'AMIHAW1811' (U.S. patent application Ser. No. 16/501,724), in the following characteristics described in Table 2 below.

TABLE 2

| Characteristic | 'AMIHAW1911' | 'AMIHAW1811' |
|---|---|---|
| General coloration of the mature foliage. | Darker shade of green than 'AMIHAW1811'. | Lighter shade of green than 'AMIHAW1911'. |
| Foliage size. | Smaller than 'AMIHAW1811'. | Larger than 'AMIHAW1911'. |
| Foliage thickness. | Thinner than 'AMIHAW1811'. | Thicker than 'AMIHAW1911'. |
| Size of the foliar protuberances. | Smaller than 'AMIHAW1811'. | Larger than 'AMIHAW1911'. |
| Abundance of foliar protuberances. | Less abundant than 'AMIHAW1811'. | More abundant than 'AMIHAW1911'. |

That which is claimed is:

1. A new and distinct variety of *Haworthia limifolia* x *Aloe vera* plant named 'AMIHAW1911', substantially as described and illustrated herein.

* * * * *